United States Patent
Eisele et al.

(10) Patent No.: US 6,273,085 B1
(45) Date of Patent: Aug. 14, 2001

(54) DRY POWDER INHALER

(75) Inventors: Robert Eisele; Karen Davies; Jeffrey Chen; Bernard Greenspan, all of San Diego, CA (US)

(73) Assignee: Dura Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/226,054

(22) Filed: Jan. 5, 1999

Related U.S. Application Data (63) Continuation of application No. 08/821,753, filed on Mar. 20, 1997, now Pat. No. 6,006,747.

(51) Int. Cl.⁷ ................................................. A61M 15/00
(52) U.S. Cl. .............................. 128/203.15; 128/203.12; 128/200.14
(58) Field of Search ........................ 128/203.15, 200.14, 128/200.23, 203.12, 203.21, 203.19

(56) References Cited

U.S. PATENT DOCUMENTS

| | | |
|---|---|---|
| 3,604,559 | 9/1971 | McCall . |
| 4,307,734 | 12/1981 | Blankenship . |
| 4,524,769 | 6/1985 | Wetterlin . |
| 4,805,811 * | 2/1989 | Wetterlin .............................. 222/337 |
| 4,971,221 | 11/1990 | Urquhart et al. . |
| 5,207,217 | 5/1993 | Cocozza et al. . |
| 5,301,666 | 4/1994 | Lerk et al. . |
| 5,327,883 | 7/1994 | Williams et al. . |
| 5,331,953 * | 7/1994 | Andersson et al. ............. 128/200.14 |
| 5,337,740 | 8/1994 | Armstrong et al. . |
| 5,388,572 | 2/1995 | Mulhauser et al. . |
| 5,388,573 | 2/1995 | Mulhauser et al. . |
| 5,415,162 | 5/1995 | Casper et al. . |
| 5,460,173 | 10/1995 | Mulhauser et al. . |
| 5,503,869 | 4/1996 | Van Oort . |
| 5,529,059 | 6/1996 | Armstrong et al. . |
| 5,577,497 | 11/1996 | Mecikalski et al. . |
| 5,590,645 | 1/1997 | Davies et al. . |
| 5,647,347 | 7/1997 | Van Oort . |
| 5,687,710 | 11/1997 | Ambrosio et al. . |
| 5,794,613 | 8/1998 | Piskorski . |
| 6,065,472 * | 5/2000 | Anderson et al. .............. 128/203.21 |

FOREIGN PATENT DOCUMENTS

| | | |
|---|---|---|
| 0 485 819 A1 | 1/1991 | (EP) . |
| 2 264 237 | 8/1993 | (GB) . |
| WO 94/06497 | 3/1994 | (WO) . |

* cited by examiner

Primary Examiner—Glenn K. Dawson
Assistant Examiner—V. Srivastava
(74) Attorney, Agent, or Firm—Lyon & Lyon LLP (57) ABSTRACT

A dry powder inhaler has a lid pivotally attached to an inhaler housing. A medicine containing cartridge is attached to the top of the housing and includes a cartridge ring with apertures for holding dry powdered medicine. A slide-groove assembly located on the underside of the lid advances the cartridge ring to a next aperture when a user first opens, then closes the lid. A venturi air passageway assembly is contained within the housing of the dry powdered inhaler. The venturi air passageway assembly includes a tapered inlet section, a throat section, and a tapered outlet section. A pressure switch is advantageously located within the housing for actuating the mixing process within the mixing chamber. During inhalation, the pressure switch contained within the housing actuates the motor driven impeller within the mixing chamber of the inhaler when the pressure within the venturi air passageway reaches a predetermined level. The pressure at which the pressure switch closes corresponds to a specifically calibrated inhalation flow rate.

19 Claims, 9 Drawing Sheets

Fig. 6 ated Mar. 20, 1997 now U.S. Pat. No. 6,006,747 filed Dec.

DRY POWDER INHALER

This application is a continuation of Ser. No. 08/821,753, filed Mar. 20, 1997 now U.S. Pat. No. 6,006,747 filed Dec. 28, 1999.

BACKGROUND OF THE INVENTION

Field of the Invention

The field of the invention is inhalers. More specifically, the invention relates to dry powder inhalers for delivering drugs in a finely divided dry powder or fluid form.

Inhalers are used to deliver drugs into a patient's lungs. Typically, an inhaler contains or provides a mixture of drugs and air or propellants. The mixture is delivered via the patient inhaling from a mouthpiece on the inhaler, for treatment of various conditions, for example, bronchial asthma. However, delivery of drugs via inhalation can be used for many other treatments, including those unrelated to lung conditions.

One well known inhaler, described in PCT application No. PCT/US93/09751 contains individual medicine doses stored within a plurality of apertures in a medicine containing cartridge. The cartridge is manually advanced to successive doses by rotating the medicine containing cartridge. However, while the above-described device has met with varying degrees of success, disadvantages still remain in indexing or advancing the cartridge within the inhaler, and in reliably delivering a precise quantity of drug from the cartridge.

U.S. Pat. Nos. 5,327,883, and 5,577,497, both incorporated herein by reference, describe an inhaler having a spinning impeller. The motor for spinning the impeller is switched on by a sail-switch. In the above design, the sail switch has a sail or flap which is moved by the flow of air caused by the patient inhaling. The mechanical movement of the flap closes the switch, thereby turning on the motor. The motor spins an impeller within a mixing chamber, resulting in drug/air mixing and drug particle deagglomeration. As the inhaler is substantially flow rate independent, and may be used at very low flow rates, the switch must be very sensitive to air flow. Although the sail-switch has performed well in the past, improvements remain to be made in switch performance.

Inhalers have also used various techniques for storing drugs to be delivered. Some inhalers have used bulk drug storage reservoirs and mechanisms for dividing out individual doses with each use. Other inhalers have used separately packaged drug doses, such as in U.S. Pat. Nos. 4,778,054 and 5,327,883. Still, reliable and consistent delivery of doses of dry powder drugs has remained as an elusive objective.

Accordingly, it is an object of the invention to provide an improved inhaler.

SUMMARY OF THE INVENTION

To these ends, the present inhaler includes a housing containing a mixing or aerosolizing chamber. A multi-dosage medicine containing cartridge is advantageously attached on the top of the housing. The cartridge has individual dosages radially spaced apart in a cartridge ring. A lid is advantageously pivotally attached to the housing and is used to index or advance the cartridge ring to a next aperture for delivery of successive drug dosages.

Also to these ends, a dry powder inhaler includes a venturi air passageway contained within an inhaler housing. The venturi air passageway preferably has a tapered inlet section, a throat section, and a tapered outlet section. A pressure switch is advantageously contained within the inhaler housing and actuates a motor which spins an impeller. When a patient inhales from a mouthpiece on the inhaler, a pressure differential develops across the venturi air passageway. When the pressure within the venturi reaches a predetermined value, the motor is turned on by the pressure switch. Accordingly, the inhaler accurately and reliably senses inhalation and switches the motor on.

Other and further objects will appear hereinafter.

BRIEF DESCRIPTION OF THE DRAWINGS

In the drawings, wherein similar reference characters denote similar elements throughout the several views.

DETAILED DESCRIPTION OF THE PREFERRED EMBODIMENTS

Figure 1A:
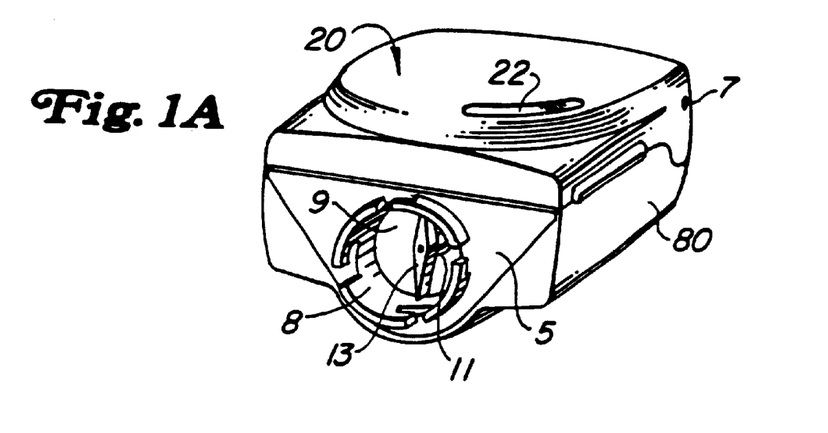
FIG. 1(a) is a perspective view of the inhaler with the detachable mouthpiece portion removed.
Figure 1B:
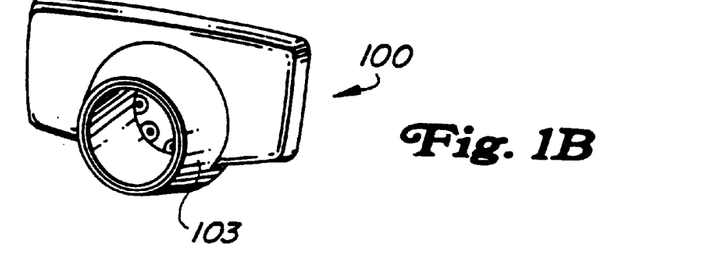
FIG. 1(b) is a front perspective view of the detachable mouthpiece used in the inhaler shown in FIG. 1(a)
Figure 1C:
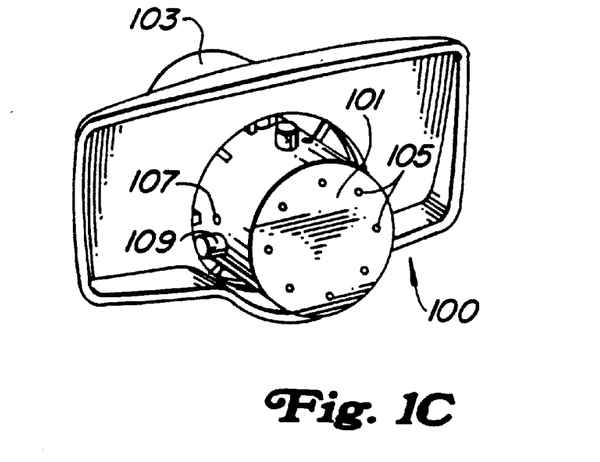
FIG. 1(c) is a perspective view of the back side of the detachable mouthpiece shown in FIG. 1(b)
Figure 2A:
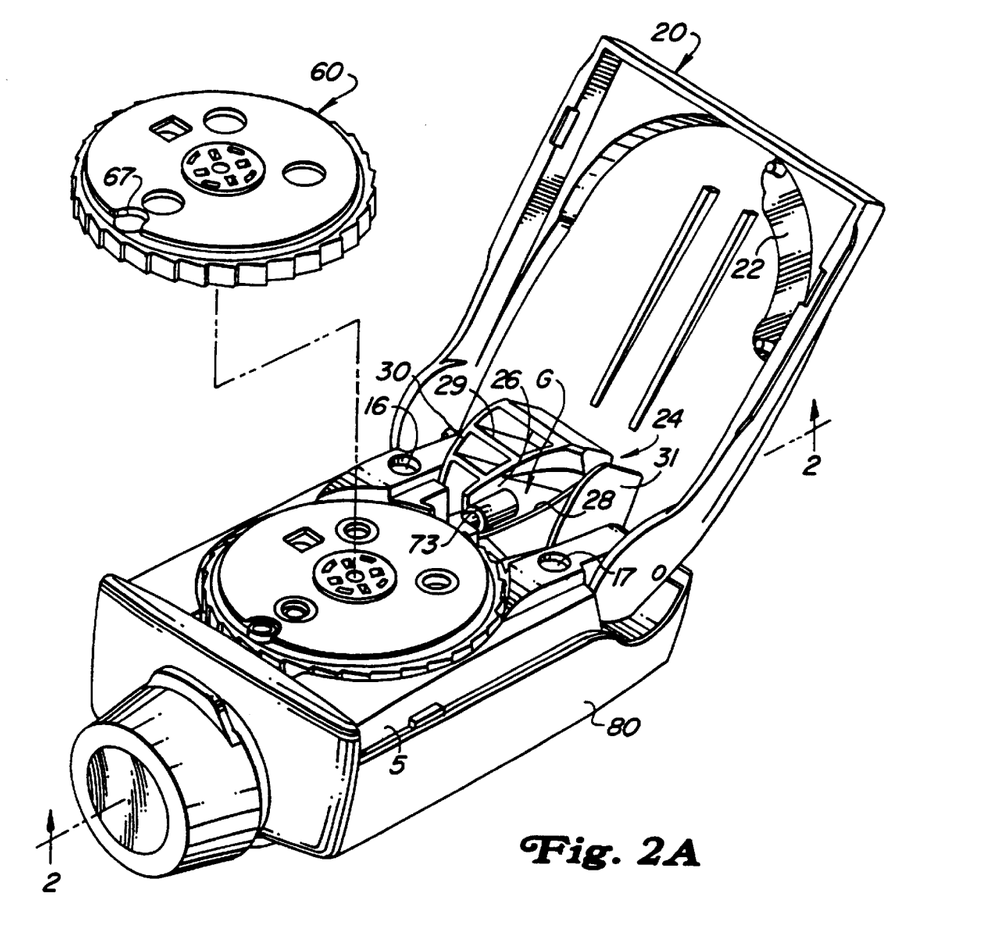
FIG. 2(a) is a perspective view of the inhaler shown in FIG. 1(a) with the lid of the inhaler in the open position, and the mouthpiece covered.
Figure 2B:
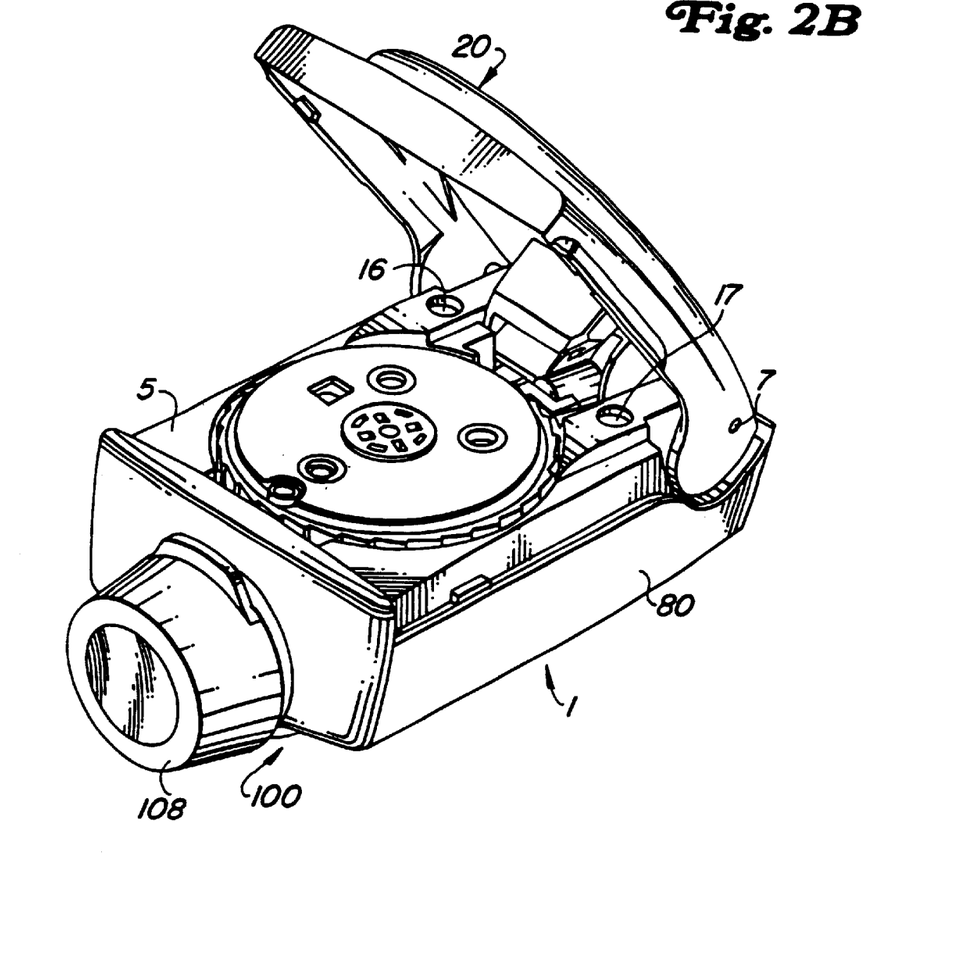
FIG. 2(b) is a perspective view of the inhaler shown in FIG. 2(a), wherein the lid is in a partially opened position.
Figure 3:
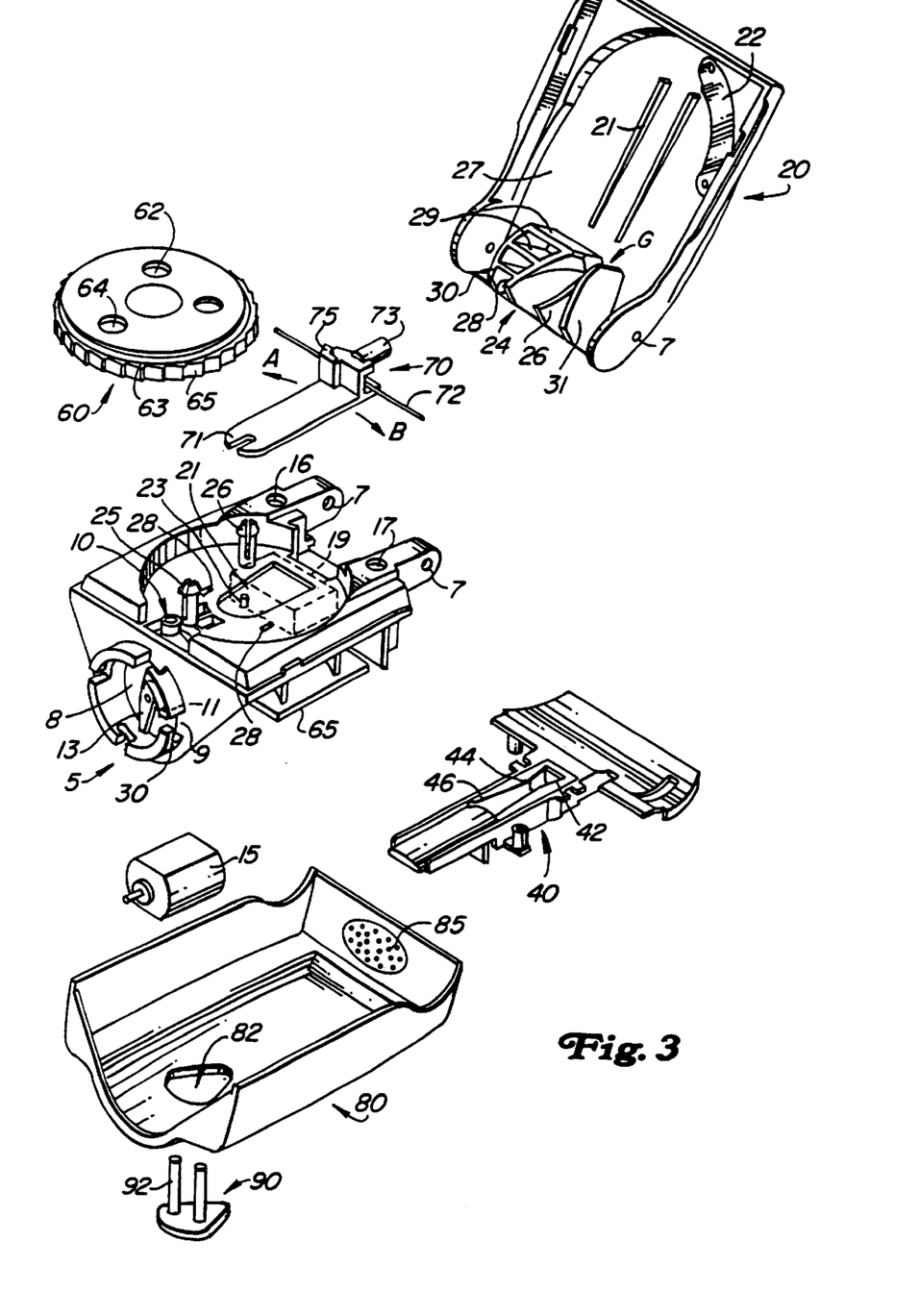
FIG. 3 is an exploded perspective view of the inhaler of FIGS. 2(a) and 2(b)

Turning now in detail to the drawings, as shown in FIGS. 1–3, a dry powder inhaler 1 includes a lid 20 pivotally mounted via hinge 7 a housing 5. Lid 20 includes a transparent window 22 for viewing individual drug dosages 67 within a medicine containing cartridge 60 supported on the housing 5. A slide groove assembly 24 located on the underside of the lid 20 includes a groove G located between a first vertical face 26 and a second vertical face 28, as shown in FIG. 2(a) and 3. Both the first vertical face 26 and the second vertical face 28 extend at an angle with respect to the longitudinal centerline of the inhaler. Ribs 29 and a vertical support wall 30 support the vertical face 28 and, a vertical support wall 31 supports the first vertical face 26. Extensions 21 help to hold a cartridge 60 down onto the housing 5, when the lid 20 is closed.

Turning now to FIGS. 1(a), 1(b), 1(c) and 3, the housing 5 includes a mixing, or aerosolizing chamber 8. Mixing chamber 8 is formed on the back side by a rear wall 9 molded in the housing 5, and on the front by the rear wall 101 of a removable mouthpiece 100, as shown in FIG. 1(c). As shown in FIG. 3, a drug port 10 on the top of the housing 5 extends into the mixing chamber 8. An opening 11 in the rear wall 9 within mixing chamber 8, allows air flow into the mixing chamber during patient inhalation. An impeller 13 within the mixing chamber 8 is attached to a shaft of an electric motor 15.

Referring still to FIG. 3, the housing 5 further includes a pair of light emitting diodes (LEDs) 16 and 17 on its top surface. LED 16 is advantageously red in color and when lit indicates to the patient that batteries (not shown) used in powering the dry powder inhaler need replacement. LED 17 is preferably a different color than LED 16, e.g., green, and indicates that the battery power is sufficient and that the number of inhalation cycles of the device (e.g., 1500 cycles) has not been exceeded. A blinking light indicates that the inhaler has sufficient battery power and remaining life cycles to deliver drug doses from two more cassettes. A circuit board 65 attached to the bottom of the housing 5 is linked to the LEDs 16 and 17, and to the batteries and to the motor, to control these functions.

Continuing to refer to FIG. 3, a lever recess 21 is located within the top surface of the housing 5. A vertical post 23 extends up from the top surface of housing 5, and is a pivot point for ratchet lever 70. The rachet lever 70 includes a forked end 71, a cylinder end 73, and a tooth 75. The ratchet lever 70 is pivotable about the vertical post 23. Its movement is limited by the edges of lever recess 21. A leaf spring 72 on the housing 5 pushes the ratchet lever 70 radially inwardly and keeps the forked end 71 against the post 23. The ratchet lever 70 slides along the leaf spring as the lid is opened and closed.

A pressure switch 19 is located on the underside of housing 5, for actuating the impeller 13 via electric motor 15. The pressure switch 19, shown in phantom in FIG. 3, preferably is an MPL-502-0.15 V available from Micro Pneumatic Logic, Inc., Ft. Lauderdale, Fla. The pressure switch 19 is linked to the motor 15.

Figure 5A:
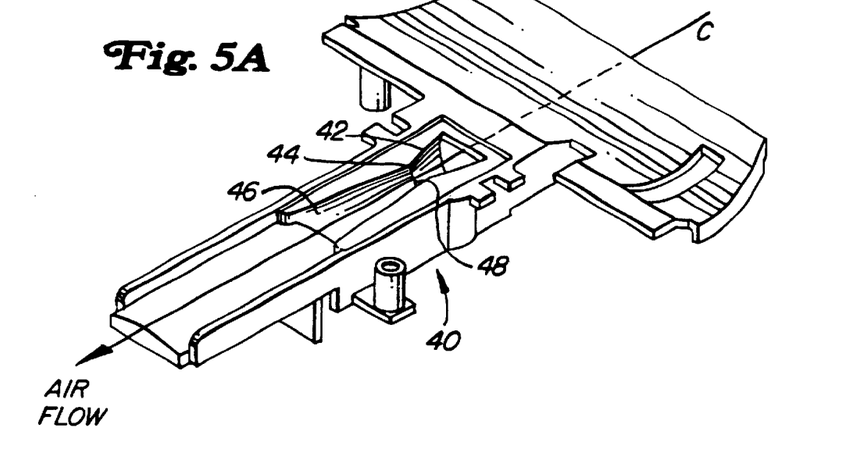
FIG. 5(a) is a perspective view of the venturi air passageway assembly shown in FIG. 3.
Figure 5B:
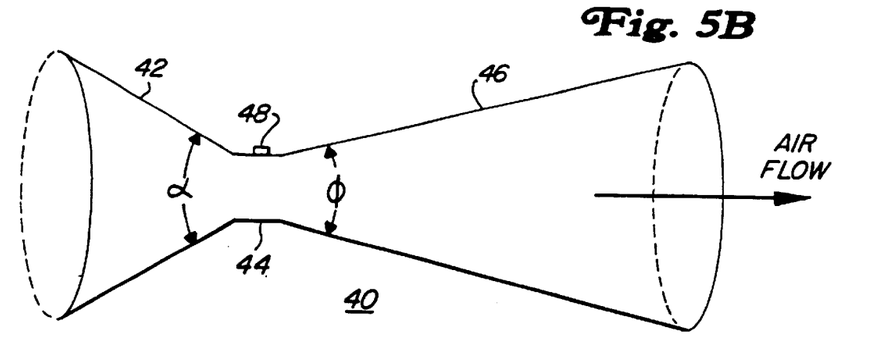
FIG. 5(b) is a geometric construction of the venturi shown in FIG. 5(a)

Referring now to FIGS. 3, 5(a), and 5(b), the dry powder inhaler includes a venturi air passageway assembly 40 preferably as a separately molded component. When the dry powder inhaler is assembled, as shown in FIGS. 2(a) and 2(b), the venturi air passageway assembly 40 is attached e.g., adhered or, heat sealed ultrasonically welded, to the underside of housing 5, forming a generally air-tight passageway from inlet holes 85 to the mixing chamber 8.

The venturi passageway assembly 40 allows for consistent and reproducible actuation of pressure switch 19. Referring to FIG. 5(b), the venturi section of the assembly 40 includes a tapered section 42 that initially receives atmospheric air when a patient inhales on the mouthpiece 100. The tapered inlet section 42 preferable has a converging angle λ within the range of approximately 20–30°, preferably about 25°. The tapered inlet section 42 can have a variety of cross-sectional profiles, including circular, semi-circular, parabolic, and the like.

The venturi air passageway further includes a throat section 44 that is continuous with tapered inlet section 42 and has a constant axial cross-sectional area. Like the inlet section 42, the throat section 44 may have a variety of cross-sectional profiles. Preferably, the throat section 44 has throat diameter as in the range of about 0.08–0.12 inches and preferably approximately 0.10 inches. The throat section may have a variable length within the range of approximately 0.03" to 0.07", preferably about 0.05". A pressure tap 48 is located within throat section 44, where pressure switch 19 measures the pressure in throat section 44 during inhalation.

Continuing to refer to FIG. 5(b), venturi air passageway assembly 40 includes a tapered outlet section 46 that is continuous with mixing chamber 8. The tapered outlet section 46 preferably has a diverging angle φ within the approximate range of 5–10°, preferably 7°. The tapered outlet section 46 can have a variety of cross-sectional profiles, including circle, semi-circular, parabolic and the like. In the preferred embodiment, the inlet, throat, and outlet are semi-circular.

Preferably, the maximum internal diameters of both the tapered outlet section 46 and the tapered inlet section 42 are equivalent. The ratio β, defined as the ratio of the throat section diameter to the maximum diameter of the tapered inlet section, should vary between ¼ and ½, and is preferably approximately ½. When β falls within the above-specified range, the pressure switch 19 can reliably and consistently activate the motor 15 under operational flow conditions.

Figure 4:
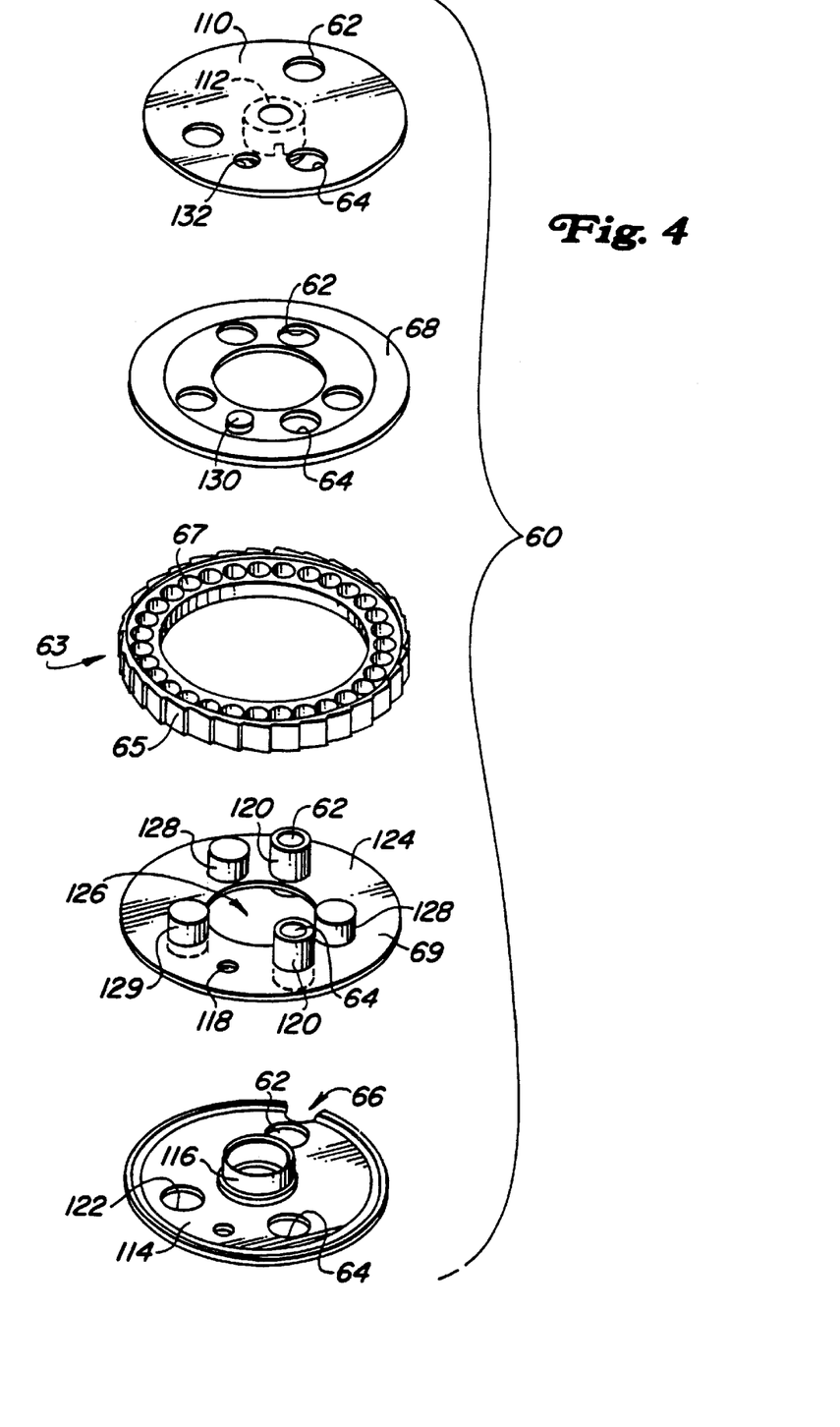
FIG. 4 is an exploded perspective view of the medicine containing cartridge assembly shown in FIG. 2A.

Referring now to FIGS. 3 and 4 a medicine containing cartridge 60 includes a cartridge ring 63 having sawtooth edges 65 located circumferentially around its perimeter. Holes 67 in the ring 63 are filled with dry powder medication. The cartridge ring 63 is sandwiched between a top seal plate 68 and a bottom seal plate 69. Both the top and bottom seal plates 68, 69 are preferably made of transparent plastic and largely prevent contamination or leakage of the powder from apertures 67. A top spring plate 110 having a slotted central hub 112 is positioned on top of the seal plate 68. A bottom spring plate 114 having a receptacle 116 is positioned under the bottom plate 69. The receptacle 116 is adapter to receive and snap-lock onto the hub 112 of the receptacle 116, to hold the ring and plates together in a sandwich construction. Anti-rotation holes 62 and 64 extend throughout the entire medicine containing cartridge 60, preventing the plates 110, 68, 69, and 114 from moving during indexing.

The bottom seal plate 69 has a hole 118 and two through-plate posts 120 which engage the anti rotation holes in the bottom spring plate 14, and maintain the hole 118 aligned over the opening 66. The top surface 124 of the bottom seal plate 69 also has two short blind posts 128 which extend up from the top surface 124, but do not protrude below the bottom seal plate 69. The top surface 124 is otherwise flat and smooth. The receptacle 116 extends up through a large clearance hole 126 in the bottom seal plate 69. A third short blind post 129 extends above and below the plate 69. A chute opening 66 in the bottom plate 69 is provided so that the apertures 67 can be accessed when brought into alignment with drug port 10 during use.

The posts 120 on the bottom seal plate 69 extend through holes 62 and 64 in the top plate 68. A step post 130 extends up from the top surface of the top plate and engages a hole 132 in the top outer plate 110, thereby aligning the plates 110, 68, 69 and 114.

The cartridge ring 63 preferably is made of Delrin. The top plate 68 and bottom plate 69 are preferably made of polycarbonate. These materials provide appropriate lubricity between their sliding surfaces as the ring 63 turns within the sandwiched plates, and better prevent migration of powder out of the drug storage holes 67.

Figure 4A:
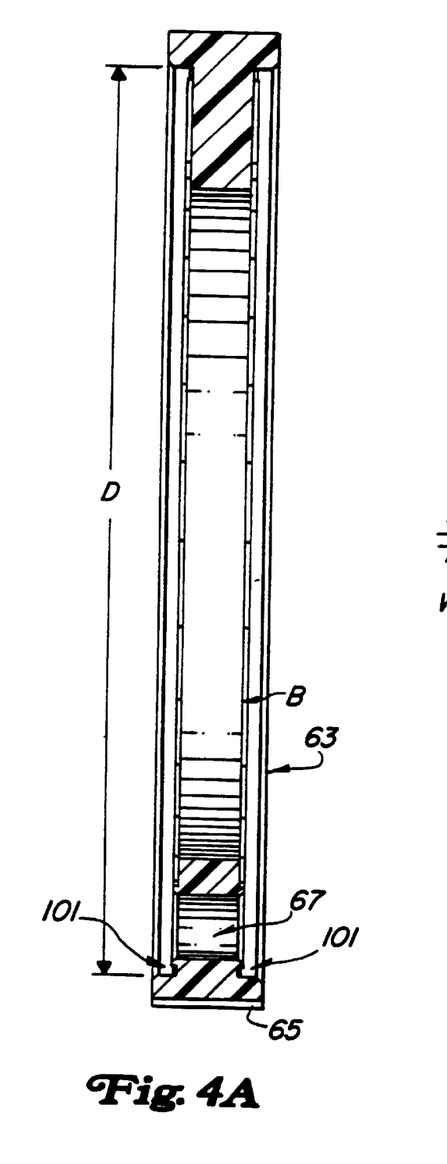
FIG. 4A is a section view of the outer ring of the cartridge shown in FIG. 4.
Figure 4B:
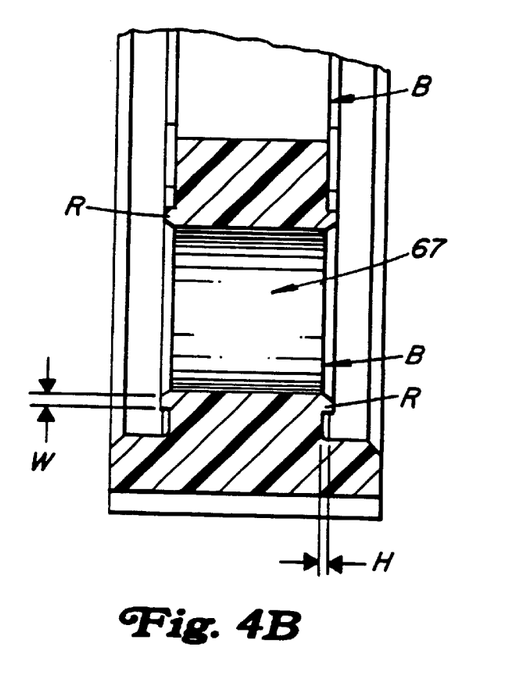
FIG. 4B is an enlarged section view of a single hole in the center ring shown in FIG. 4.
Figure 4C:
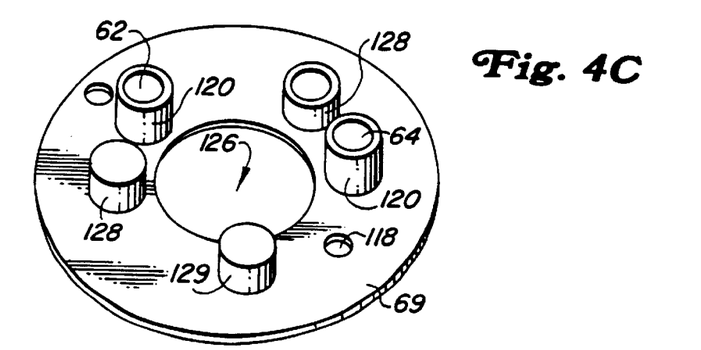
FIG. 4C is an enlarged top perspective view of the bottom seal plate shown in FIG. 4.
Figures 4D, 4E, 4F:
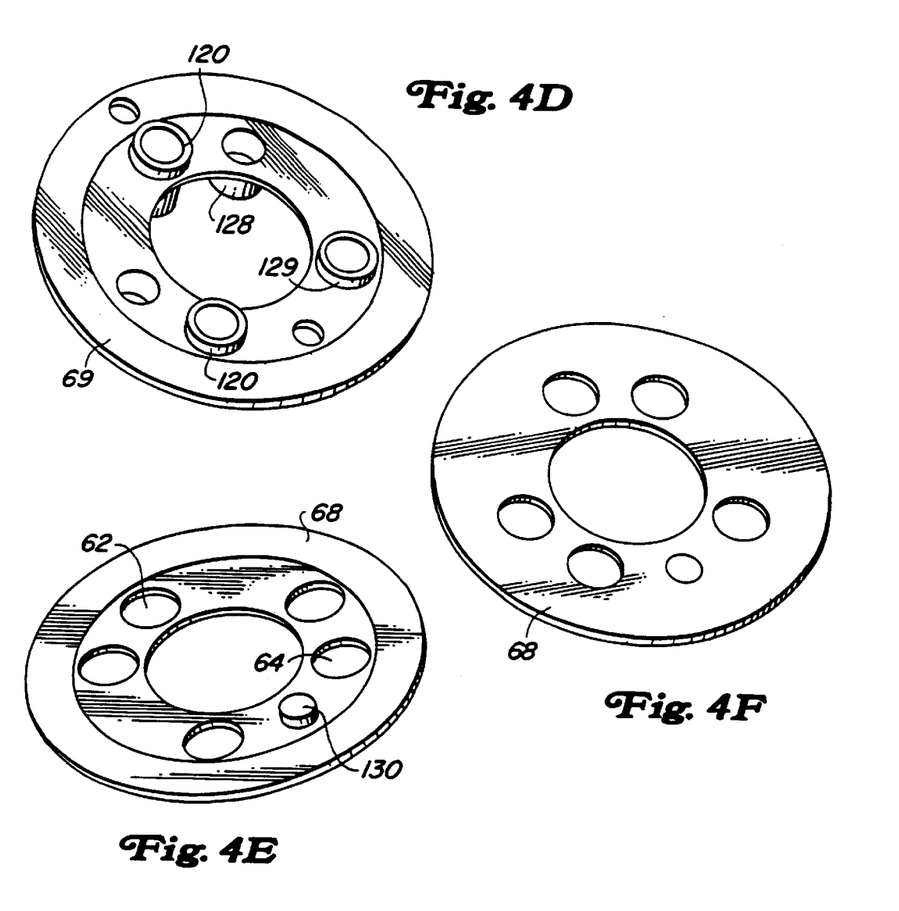
FIG. 4D is a bottom perspective view thereof.
FIG. 4E is an enlarged top perspective view of the top seal plate shown in FIG. 4.
FIG. 4F is a bottom perspective view thereof.
Figure 4G:
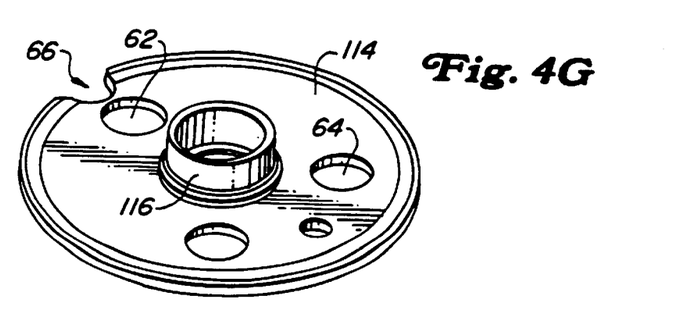
FIG. 4G is an enlarged top perspective view of the bottom spring plate shown in FIG. 4.
Figure 4H:
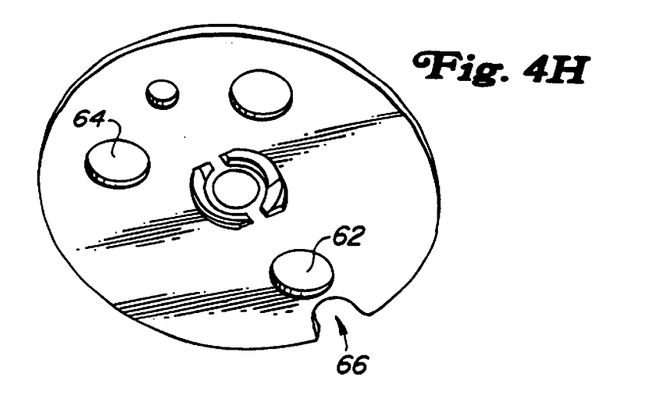
FIG. 4H is a bottom perspective view thereof.
Figure 4I:
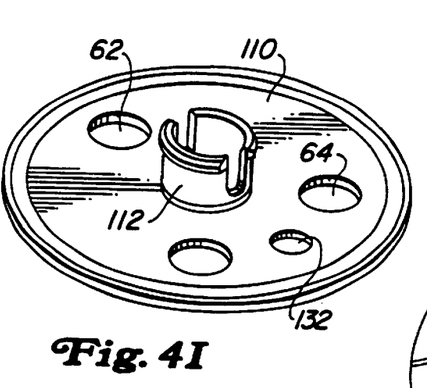
FIG. 4I is an enlarged top perspective view of the top spring plate shown in FIG. 4.
Figure 4J:
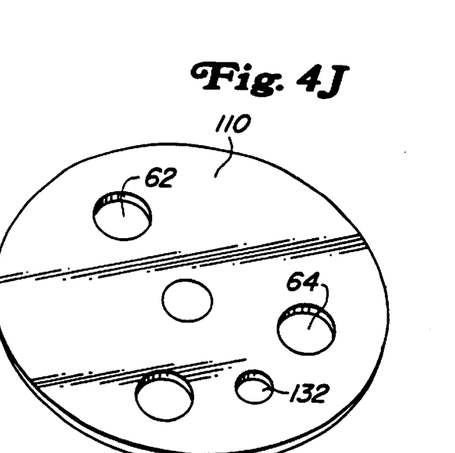
FIG. 4J is a bottom view thereof.

As shown in FIGS. 4A and 4B, the ring 63 has a recess 101 on its top and bottom, with a diameter D. The seal plates have a matching (nominally smaller) diameter and center themselves on the ring 63 when assembled. A lip or rim R is formed around each hole 67, as shown in FIG. 4B. The holes 67 are sealed via the seal plates engaging the rims R, which rise above the base ring surface B by a distance H, about 0.2 mm (0.008 in). The width W of the rim R is also about 0.2 mm. The rim R acts as a wiper or scraper on the seal plates, and helps to seal the powder in the holes 67, before, during, and after each movement of the ring.

The spring plates 110 and 114 are independent of the seal plates. The spring plates exert a clamping or normal force on the seal plates, to hold the seal plates flat against the ring 63, and specifically against the rims R, on top and bottom. This force is created and maintained by the snap engagement of the hub 112 into the receptacle 116, during assembly. The 5-layer sandwich cartridge can therefore reliably contain and deliver accurate doses of drug powder.

Referring now to FIG. 3, to load the medicine containing cartridge 60, the patient aligns anti-rotation holes 62 and 64 over slotted anti-rotation pegs 25 and 26 and presses the cartridge down. Tabs on the ends of pegs 25 and 26 spring outwardly after clearing the top spring plate 110 of the cartridge 60, and securely fasten the cartridge 60 to the housing 5.

Referring still to FIG. 3, a housing cover assembly 80 is attached to the under-side of housing 5, enclosing the motor 15, the venturi air passageway assembly 40, the batteries and the circuit board 65. An ejection button recess 82 containing an ejection button 90 is located on the bottom surface of the housing cover assembly 80. The ejection button 90 includes a pair of ejection prongs 92 for ejecting the cartridge assembly 60 from the housing. To eject cartridge 60, a patient merely presses the ejection button 90 with sufficient force to release the cartridge 60 from pegs 25 and 26. The prongs 92 push against the solid flat bottom surface of the bottom spring plate 114.

Referring now to FIGS. 1(a), 1(b), and 1(c), a detachable mouthpiece 100 includes a tapered mouth portion 103. The rear-wall 101 is located on the back of the detachable mouthpiece 100. A plurality of holes 105 in the rear-wall 101 allow the air-drug mixture to flow from the mixing chamber 8 into the mouthpiece 100 during inhalation. Radial holes 107 are positioned circumferentially around the back portion of the detachable mouthpiece 100. Referring briefly to FIGS. 2(a) and 2(b), a removable mouthpiece cover 108 is press-fit on the mouthpiece 100 when the inhaler is not in use.

Radial pins 109 on the back of mouthpiece 100, which engage grooves 30 on housing 5, enable a patient to easily remove and re-attached mouthpiece 100 to housing 5, for cleaning.

To advance, or index the cartridge 60 to a next, successive dose, a patient simply first opens, then closes lid 20 of the dry powder inhaler. Referring to FIGS. 2(a), 2(b), and 3, when a patient begins to open the lid 20 to a position shown in FIG. 2(a), the ratchet lever 70 begins to pivot around vertical post 23 on the housing 5 due to the mechanical engagement of the cylinder end 73 with the slide-groove assembly 24 contained in the lid 20. As the lid is opened, the cylinder end 73 is progressively pushed in the direction of arrow A in FIG. 3 by the sliding contact with the first vertical face 26 of lid 20. The ratchet lever 70 simultaneously moves radially outwardly against the inward acting force of the spring 72, as the tooth 75 rides up and over a sawtooth on the cartridge ring. The forked end 71 allows radial movement away from the post 23. Friction prevents the ring from moving with the tooth 75 on the ratchet lever 70.

When lid 20 is fully opened to a position shown in FIG. 2(a), the tooth 75 has passed over a sawtooth and moved back radially inwardly to form a mating, or matching fit with a sawtooth edge 65 of cartridge ring 63. The spring 72 drives the tooth portion inwardly behind the sawtooth after it has cleared the sawtooth. Once the matching connection has been made, the patient closes the lid 20, to the position shown in FIG. 1(a). When pivoting lid 20 towards the closed position, the tongue 73 of ratchet lever 70 is progressively pushed in the direction of arrow B due to the sliding contact with the second vertical face 28.

As the tooth 75 of the lever ratchet 70 is now in mating contact with sawtooth edge 65, the sawtooth edge 65 and cartridge ring 63 likewise rotate in the direction of arrow B driven by the interaction of the tongue 73 in the slide groove 24. The plates 68, 69, 110 and 114 of the cartridge 60 remain fixed at all times on the pegs 25 and 26. When the lid 20 has closed to the position shown in FIG. 1(a), cartridge ring 63 has indexed, or advanced one aperture 67, so the next dose can be delivered to the patient.

In use, the dry powder inhaler is held in an upright position as shown in FIG. 1(a). Prior to inhalation, a patient advances, or indexes the medicine containing cartridge 60 to move the next dose into the delivery position by opening and closing the lid 20. A new aperture 67 containing powdered drug is moved into alignment over drug port 10. The aperture 67 and powdered drug containing therein are no longer sandwiched between the top plate 68 and bottom plate 69 because chute hole 66 in the bottom plate 69 allows access to mixing chamber 8.

After advancing the cartridge, the user places the tapered mouthpiece 103 of detachable mouthpiece 100 into the mouth and inhales. As the user inhales, air is drawn through inlet holes 85 into the venturi air passageway assembly 40. The velocity of air flowing through the throat section 44 increases, causing a corresponding decrease in pressure in throat section 44 consistent with Bernoulli's principle.

Figure 6:
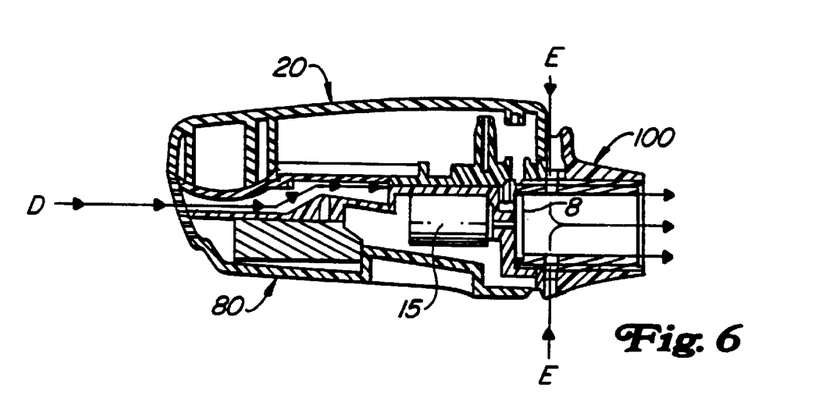
FIG. 6 is a partial section view taken along the line 2—2 of FIG. 2(a).

FIGS. 5(a) and 6 illustrate the path of air through the inhaler and venturi 40. Arrow C in FIG. 5(a) shows the air path from the atmosphere through the venturi air passageway assembly 40. FIG. 6 illustrates this same flow path by arrow D, only this view shows a cross-sectional view of the flow in the entire inhaler.

The reduced pressure in the throat section 44 is detected via a pressure tap 48 or tube connecting the throat section 44 to the pressure switch 19. Accordingly, when the pressure drop across throat section 44 reaches a sufficient magnitude, the pressure switch 19 closes, thereby turning on motor 15. The spinning impeller attached to a shaft of motor 15 begins spinning within mixing chamber 8. Preferably, the pressure switch 19 closes when the flow rate in mouthpiece 100 exceeds the approximate range of 4–8 liters/minute, a very low threshold which virtually all patients can meet or exceed using the inhaler. The design of the venturi allows independent selection of the flow rate which actuates the motor 15. The venturi also serves as a control point for the flow resistance of the inhaler, preferably creating a resistance of about 0.1–0.2 $(cm\ H_2O)^{1/2}$. The value of the pressure drop at the venturi may also be used to determine the inhalation flow rate. This information can be recorded, displayed or used to tell the patient if the proper rate was achieved.

Both inhalation and turbulence created from spinning impeller 13 pull air exiting the tapered outlet section 46 into mixing chamber 8 via an opening 11 located on the rear-wall 9 of the mixing chamber 8. In addition, the same inhalation and turbulence causes powdered drug stored within aperture 67 to transfer to mixing chamber 8 via drug port 10. Air and drug are mixed in the mixing chamber by the spinning impeller.

Referring now to FIG. 1(c), powder laden air passes out of the mixing chamber 8 through outflow holes 105 located in the rear-wall 101 of mouthpiece 100 and into the interior of the mouthpiece 100 and from there into the patients lungs.

Thus, a novel inhaler has been shown and described. Various changes and modifications can of course be made and various equivalents and substitutions can be used, without departing from the spirit and scope of the present invention. The invention, therefore, should not be restricted, except by the following claims.

We claim:

1. A medicine containing cartridge for use with an inhaler, comprising:
   a cartridge ring having a top side and a bottom side;
   a plurality of spaced apart cartridge ring holes extending through the cartridge ring for holding a dry powder;
   a top seal plate on the top side of the cartridge ring;
   a bottom seal plate on the bottom side of the cartridge ring;
   a top spring plate overlying the top seal plate; and
   a bottom spring plate underlying the bottom seal plate.

2. The cartridge of claim 1 further comprising sawtooth edges located circumferentially around the perimeter of the cartridge ring.

3. The cartridge of claim 1 wherein the top and bottom seal plates and spring plates are made of transparent plastic.

4. The cartridge of claim 1 wherein one of the top and bottom spring plates has a hub and the other has a receptacle adapted to snap lock onto the hub, to hold the cartridge ring, seal plates, and spring plates together in a sandwich construction.

5. The cartridge of claim 1 further comprising a pair of anti-rotation holes extending through the seal plates and the clamp plates.

6. The cartridge of claim 1 further comprising a delivery hole in the bottom seal plate and a chute opening in the bottom spring plate with the cartridge ring indexable to move substantially each of the cartridge ring holes sequentially into alignment over the delivery hole, and so that a cartridge ring hole aligned over the delivery hole is open on the bottom side, but remains closed on the top side by the top seal plate.

7. The cartridge of claim 1 wherein the cartridge ring comprises Delrin and the top and bottom seal plates comprise polycarbonate, to provide an appropriate lubricity between their sliding surfaces.

8. The cartridge of claim 1 wherein the cartridge ring includes a top recess and a bottom recess adapted to receive the top and bottom seal plates.

9. The cartridge of claim 7 further comprising a rim formed around each hole on the top side and the bottom side of the cartridge ring with the rims in sliding contact with the seal plates.

10. The cartridge of claim 9 wherein the lip has a height of about 0.2 mm and a width of about 0.2 mm.

11. A cassette for holding a pharmaceutical dry powder comprising:
    a top spring plate having a central hub;
    a top seal plate having a central opening;
    an annular cartridge ring having a top side and a bottom side with a plurality of substantially equally spaced apart openings extending through the annular cartridge ring, and with substantially each opening containing a dose of a dry powder pharmaceutical, and having a rim around it at the top side and the bottom side;
    a bottom seal plate having a central opening; and
    a bottom spring plate having a receptacle around a central opening;
    the receptacle on the bottom spring plate extending through the central openings in the bottom seal plate, the annular cartridge ring, the top seal plate, and engaging the central hub in the top spring plate, thereby holding the top spring plate, the top seal plate, the annular cartridge ring, the bottom seal plate, and the bottom spring plate together into a 5-layer construction with the annular cartridge ring rotatable within the 5-layer construction, while the top and bottom seal plates and spring plates remain fixed in place, and with substantially each rim in sliding contact with a seal plate.

12. The cassette of claim 11 further comprising a pair of anti-rotation holes in the bottom spring plate, the bottom seal plate, the top seal plate and the top spring plate.

13. The cassette of claim 11 further comprising a step post on the top seal ring extending into an alignment hole on the top spring plate.

14. The cassette of claim 12 further comprising a pair of posts on the bottom seal plate around the anti-rotation holes in the bottom seal plate, the posts extending into the anti-rotation holes in the bottom spring plate, the top seal plate, and the top spring plate.

15. The cassette of claim 11 further comprising a chute opening at the perimeter of the bottom spring plate, and a hole in the bottom seal plate aligned with the chute opening.

16. The cassette of claim 11 wherein the top spring plate and the bottom spring plate clamp the top seal plate and the bottom seal plate, respectively, against the cartridge ring.

17. A dry powder inhaler cartridge comprising:
    a top spring plate having a central hub, an alignment hole, and a pair of anti-rotation holes;
    a top seal plate having a step post engaging the alignment hole in the top spring plate, and having a central opening and a pair of anti-rotation holes;
    a cartridge ring having a plurality of openings therethrough and having a central opening;
    a bottom spring plate having a central opening, a plurality of posts, a pair of anti-rotation holes, and with one of the plurality of posts around each of the anti-rotation holes;
    a bottom spring plate having a receptacle around a central opening;
    the central hub and the receptacle engaged together clamping the top and bottom spring plates and the top and bottom seal plates against the cartridge ring, and the posts around the anti-rotation holes on the bottom spring plate extending into the anti-rotation holes in the top spring plate, the top seal plate, and the bottom spring plate.

18. The cartridge of claim 17 wherein the plurality of posts on the bottom seal plate includes at least three posts arranged on a common circle and laterally holding the cartridge ring in position.

19. A medicine containing cartridge for use with an inhaler, comprising:

a cartridge ring;

a plurality of spaced apart cartridge ring holes extending through the cartridge ring, with substantially each cartridge ring hole containing a dose of dry powder medicine;

a top plate on one side of the cartridge ring;

a bottom plate having a delivery hole on the other side of the cartridge ring and attached to the top plate;

with the top plate closing off the top end of each cartridge ring hole containing a dose of dry powder;

with the cartridge ring rotatable relative to the top and bottom plates to bring substantially each of the cartridge ring holes containing a dose of dry powder into alignment over the delivery hole to allow the dose of dry powder to be removed from the cartridge for inhalation by a patient, while the top end of that cartridge ring hole remains closed off by the top plate.

* * * * *